United States Patent

Tseng et al.

[11] Patent Number: 5,672,634
[45] Date of Patent: Sep. 30, 1997

[54] CROSSLINKED PVP-I2 FOAM PRODUCT

[75] Inventors: Susan Y. Tseng, Staten Island, N.Y.; Philip F. Wolf, Bridgewater, N.J.

[73] Assignee: ISP Investments Inc., Wilmington, Del.

[21] Appl. No.: 774,064

[22] Filed: Dec. 23, 1996

[51] Int. Cl.$^6$ .................................................. C08J 9/36
[52] U.S. Cl. ............................................. 521/53; 521/142
[58] Field of Search ............................... 521/53, 142

[56] References Cited

U.S. PATENT DOCUMENTS 5,242,985  9/1993  Shih et al. .................... 525/356
5,409,697  4/1995  Immer et al. .................. 530/311

*Primary Examiner*—Morton Foelak
*Attorney, Agent, or Firm*—Walter Katz; Marilyn J. Maue; Joshua J. Ward

[57] ABSTRACT

A crosslinked PVP-I$_2$ foam product, useful as an iodophor, contains about 0.1–2% crosslinker and about 16–18% total inorganic iodine.

4 Claims, No Drawings

CROSSLINKED PVP-I2 FOAM PRODUCT

BACKGROUND OF THE INVENTION

1. Field of the Invention

This invention relates to polyvinylpyrrolidone (PVP)-iodine (I) products, i.e. (PVP-$I_2$), and, more particularly, to a crosslinked PVP-$I_2$ foam product suitable for use as an iodophor.

2. Description of the Prior Art

There has been a continuing effort to provide germicidal iodine compositions which are stable and easy to manufacture. For example, PVP is a well known carrier for $I_2$, and complexes of PVP and $I_2$, known as iodophors, are described in U.S. Pat. No. 5,409,697, and in the several references cited therein, as well as in U.S. Pat. Nos. 3,136,755; 3,907,720; 4,128,633; 5,152,987 and 5,158,768.

Shih, in U.S. Pat. No. 5,242,985, described a strongly swellable, moderately crosslinked PVP-iodine complex in the form of a free-flowing, fine, lightly yellow powder. The polymers were made by precipitation polymerization in cyclohexane. Iodination was carried out in isopropanol. These omplex powders formed an aqueous gel in water which released iodine slowly.

PVP hydrogels have been described in U.S. Pat. Nos. 5,336,697; 5,354,823; 5,360,883 and 5,362,796.

SUMMARY OF THE INVENTION

What is described herein is a crosslinked PVP-$I_2$ foam product, which is 0.1–2% crosslinked and contains about 16–18% total inorganic $I_2$.

Such a crosslinked PVP-$I_2$ foam product is made herein by the steps of forming a crosslinked PVP polymer in the form of a hydrogel which is substantially free of residual monomer and non-crosslinked PVP, then conditioning the hydrogel with moisture and acid, and, finally reacting the conditioned polymer with iodine crystals. Preferably, iodination is carried out at about 45° C. for about 3–12 hours, and then at about 90° C. for about 6–12 hours.

DETAILED DESCRIPTION OF THE INVENTION

The crosslinked PVP-$I_2$ foam product of the invention is made by first forming a shaped crosslinked PVP hydrogel by polymerization of vinylpyrrolidone (VP) monomer in water in the presence of a crosslinker such as 1-vinyl-3-(E)-ethylidene pyrrolidone (EVP), and an initiator such as Lupersol® 11 or Lupersol® 554, at a temperature of about 70°–110° C., for a period of about 3 hours. The rubbery hydrogel product then was purified by continual washing with a large volume of water to remove residual VP monomer and any water-soluble, non-crosslinked PVP. Then the preshaped hydrogel was subjected to freeze-drying to remove excess water and form a rigid, cellular or foamed polymer product. After conditioning the foam with moisture and acid, it was iodinated with solid iodine crystals at about 45° C. for about 3–12 hours, and then at about 90° C. for an additional 6–12 hours. The product was a crosslinked PVP-$I_2$ foam, containing about 0.1–2% crosslinker and about 16–18% by wt. total inorganic $I_2$, which is brown in appearance, and shows advantageous mucoadhesive properties.

EXAMPLE 1

Preparation of Shaped Crosslinked PVP Foam
(Polymerization)

A homogeneous solution of 19.0960 g of N-vinylpyrrolidone (VP), 0.9078 g of a mixture of 8.85% EVP and 91.15% VP, 80 g of distilled water and 0.3311 g of tert-butylperoxy pivalate (Lupersol® 11) was prepared and introduced into 50 ml beakers, (7 g of solution per beaker). The beakers then were placed under a blanket of nitrogen in a temperature controlled vacuum oven where a reduced pressure of 20–30 mm Hg was maintained. Without agitation, the solutions in this closed system were heated at 70° C. for 2 hours and then at 110° C. for an hour. When the reaction was completed, the materials were allowed to cool to room temperature.

The resultant rubbery products were removed from the beakers and added to about 500 volumes of distilled water for 15 hours with simultaneous removal and replacement of the water until the mother liquor was free of residual monomer and soluble, non-crosslinked PVP. During this solvent digestion step, the rubbery products swelled into a clear, transparent, disk-shaped hydrogel of crosslinked PVP polymer. This preshaped hydrogel then was subjected to freeze-drying. The resulting rigid cellular product was a shaped, light weight, compressible, crosslinked PVP polymer foam.

EXAMPLE 2

Preparation of Crosslinked PVP-$I_2$ Foam Product
(Iodination)

10 g of the foamed polymer of Example 1 was conditioned with moisture water and formic acid so that the foamed polymer contained approximately 7 to 10% water and 0.005 to 0.01% formic acid. In a sealed container, 1.80 g of iodine crystals was added to the thus-conditioned polymer product. The mixture then was tumbled at 45° C. for 10 hours, thereafter at 90° C. for 12 hours, and finally it was cooled to room temperature. The product was a brown color, light-weight, foamed, PVP-Iodine complex which was about 0.4% crosslinked and contained 16–18 wt. % total inorganic iodine and possessed excellent mucoadhesive properties.

While the invention has been described with particular reference to certain embodiments thereof, it will be understood that changes and modifications may be made which are within the skill of the art. Accordingly, it is intended to be bound only by the following claims, in which:

What is claimed is:

1. A process of making a crosslinked PVP-$I_2$ foam product which comprises forming a shaped crosslinked PVP polymer hydrogel substantially free of residual monomer and non-crosslinked PVP, conditioning the hydrogel with moisture and acid, and then reacting the conditioned polymer with iodine crystals.

2. A process according to claim 1 wherein said product is 0.1–2% crosslinked and contains about 16–18% total inorganic $I_2$.

3. A process according to claim 1 wherein said iodine is reacted at about 45° C. for about 3–12 hours, then at 90° C. for about 6–12 hours.

4. A process according to claim 1 in which the shaped crosslinked PVP hydrogel is made by polymerization of VP monomer in water in the presence of EVP as crosslinker and an initiator.

* * * * *